United States Patent
Rashman et al.

[11] Patent Number: 6,019,730
[45] Date of Patent: Feb. 1, 2000

[54] GLOW BLOOD PRESSURE SETS

[75] Inventors: Richard Rashman, Los Angeles; Dennis Shick, Burbank, both of Calif.

[73] Assignee: Prestige Medical Corporation, Northridge, Calif.

[21] Appl. No.: 08/967,408

[22] Filed: Nov. 11, 1997

[51] Int. Cl.[7] ...................................... A61N 5/00
[52] U.S. Cl. .................. 600/490; 600/494; 128/898; 40/124.01; 40/541
[58] Field of Search ............................ 600/490, 494–495; 40/124.01–124.02, 541–544

[56] References Cited

U.S. PATENT DOCUMENTS 5,602,445  2/1997  Solanki et al. ............................ 313/503

Primary Examiner—Cary O'Connor
Assistant Examiner—Michael Astorino
Attorney, Agent, or Firm—Blakely Sokoloff Taylor & Zafman

[57]  ABSTRACT

A blood pressure set allow for the reading of blood pressures to determine the medical condition of a patient. However, in certain situations, it is inconvenient or sometimes impossible to read the pressure readings on the gauge. For instance, in a dark hospital room where the patient is sleeping, it is necessary to turn on the light and read the gauge causing inconvenience or in an outside emergency at night, due to poor lighting, the gauge is impossible to read. Here, a blood pressure set is described which allows for easy reading of the gauge in dark conditions.

16 Claims, 4 Drawing Sheets

GLOW BLOOD PRESSURE SETS

BACKGROUND OF THE INVENTION

1. Field of the Invention

The present invention relates to the field of blood pressure sets. In particular, the invention relates to a gauge face plate of the blood pressure set that is photoluminescent.

2. Description of the Related Art

Blood pressure is a pressure exerted by the blood on the walls of the arteries in which the pressure is dependent on the action of the heart. This blood pressure could be measured if a gauge were to be inserted anywhere along the arteries of the person's body. Such reading is desirable in that one could determine whether the person being measured has a high blood pressure or a low blood pressure and thus determining the medical condition of the person. In other situations, for instance, in an emergency, a reading of the blood pressure could readily determine if the blood had been lost through hemorrhage. Normally, there are two blood pressures that are read. One is measured during the contraction of the heart which is the higher one and is called systolic or maximum pressure. The other pressure is measured during the dilatation of the heart which is the lower pressure called diastolic pressure.

While conventional blood pressure sets allow for the readings of these two blood pressures, in certain situations, it is inconvenient or sometimes impossible to read the pressure readings on the gauge. For instance, in a dark hospital room where the patient is sleeping, it is necessary to turn on the light to read the gauge and obtain the blood pressure readings. This results in the patient being exposed to unnecessary lighting causing inconvenience. In another situation, blood pressures may have to be measured in an emergency, such as a car accident victim at night. However, due to the poor lighting, the readings on the gauge face plate may not be readable without additional light.

One prior method involves marking the numbers on the face plate of a device such as a wristwatch with a fluorescent ink. However, such method is undesirable because the light emitted in the darkness is far from satisfactory due to low brilliance and quick decay of the light emission. In some cases, the fluorescent ink does not work at all in a dark room or outside on a dark night. Accordingly, there is a need for a blood pressure set that allows for the easy reading of the face plate of the gauge in dark situations, such as dark hospital rooms or emergencies at night.

SUMMARY OF THE INVENTION

The present invention pertains to a blood pressure set with the entire face plate of the gauge being treated with a photoluminescent material so that the entire gauge face plate glows in the dark. This allows medical personnel to easily read the blood pressures of the patient in both a dark hospital room or outside at night in emergency situations without using additional light. Photoluminescent material is a material which absorbs and stores light energy when excited by natural or artificial light, such as sunlight or fluorescent light. Once excited, it will gradually and continuously release absorbed energy in the form of light emissions for a certain period of time after the exciting sources have been removed. The process can be repeated several times without a change in the property of the material. When the entire face plate of the gauge is treated with a photoluminescent material, the glow of the entire gauge face plate will greatly aid medical personnel in taking a patient's blood pressure without disturbing the patient in a hospital room or in an emergency situation where there is no lighting. Other aspects and advantages of the invention will become apparent from the following more detailed description taken in conjunction with the accompanying drawings.

DETAILED DESCRIPTION OF THE INVENTION

Figure 1:
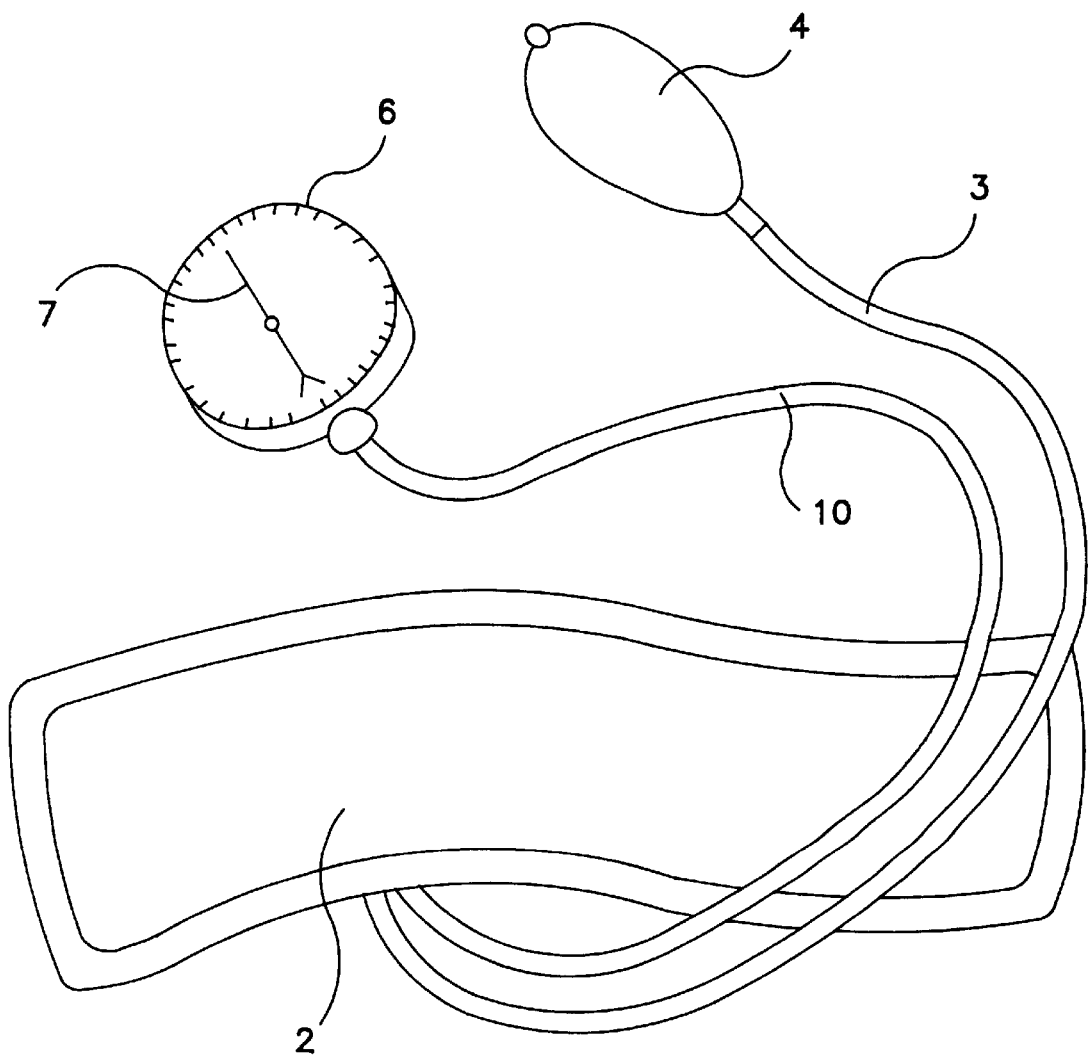
FIG. 1 illustrates an exemplary blood pressure set.
Figure 2:
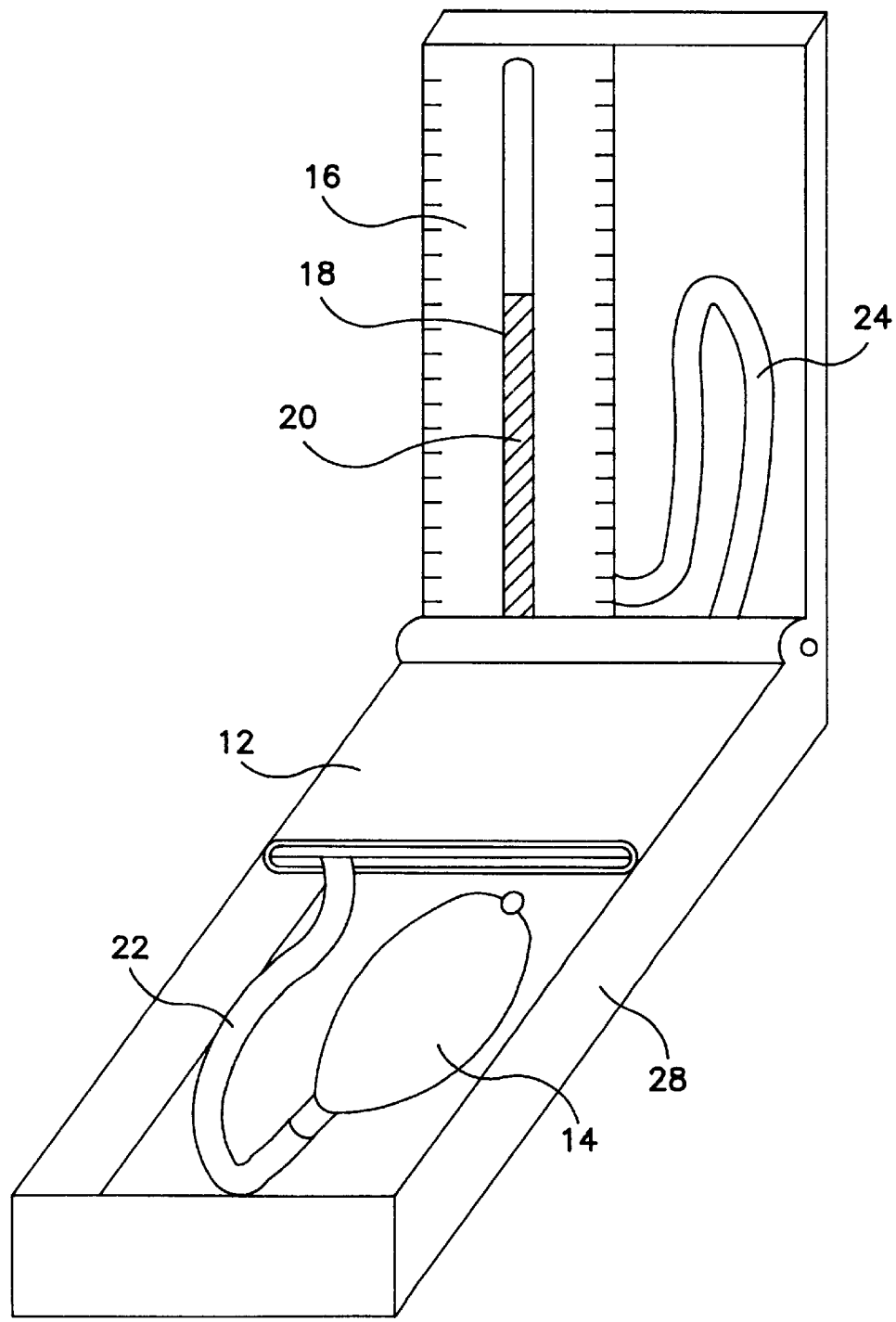
FIG. 2 illustrates an exemplary desk top mercurial sphygmomanometer.

As shown in the drawings for the purposes of illustration, the present invention pertains to blood pressure sets. FIGS. 1–2 illustrate examples of blood pressure sets, however, it will be understood by one skilled in the art from reading the disclosure that the invention may be practiced with any type of blood pressure sets.

FIG. 1 shows an exemplary blood pressure set. Typically, a blood pressure set includes an aneroid embedded in a cuff 2 wherein the cuff 2 is fastened about the arm. The cuff 2 is inflatable to assert pressure on the artery within the arm resulting in the aneroid measuring the blood pressure in the artery. Two tubes 8, 10 protrude from the cuff 2 whereby one tube 8 is connected to a bulb 4 for inflating the cuff 2. The bulb is only one means of inflating the cuff and other means may be used such as an air compressor. The other tube 10 is connected to a gauge 6 for the blood pressure readout of the patient. In this example, the gauge is a dial gauge with the readings indicated by an indicator needle.

FIG. 2 illustrates another exemplary blood pressure set. In this instance, the blood pressure set is known as a desktop mercurial sphygmomanometer. Like the blood pressure set above, the mercurial sphygmomanometer has an aneroid within a cuff 12 with two tubes 22, 24 protruding wherein one tube 22 is connected to a bulb 14. Instead of a dial gauge, the mercurial sphygmomanometer utilizes a tube 18 containing a calibrated liquid such as mercury 20 to which the other tube 24 is connected. The tube 18 is supported by the face plate 16. The blood pressure measured by the aneroid causes the calibrated liquid 20 in the tube 18 to raise up corresponding to the measured blood pressure.

Figure 3:
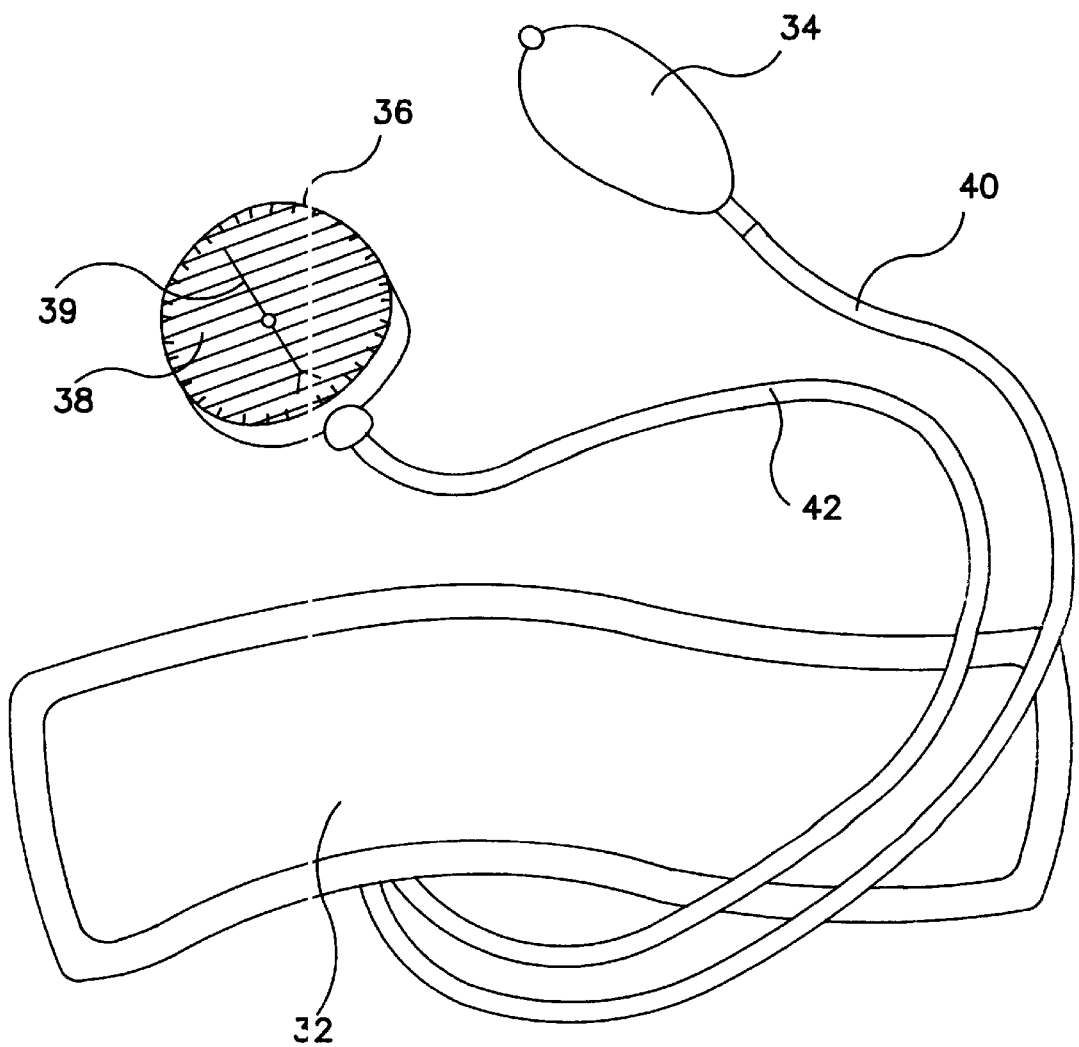
FIG. 3 illustrates an exemplary embodiment of the present invention.

FIG. 3 shows an embodiment of the present invention. The shaded area 38 on the face of the gauge 36 depicts a coating of photoluminescent material. Photoluminescent material is a material which absorbs and stores light energy when shined upon by natural or artificial light sources, such as sunlight or fluorescent light. Once excited, it will gradually and continuously release absorbed energy as of visible rays for a long time period of time after the exciting sources are removed. This process can be repeated many times without perceivable changes of its own properties. Typically, photoluminescent materials emit a yellowish-green glow. However, other colors in the range of daylight are available, examples being, yellow, orange, orange-yellow, red, pink, rose, blue and so forth.

In the exemplary blood pressure set, the photoluminescent material is coated over the gauge face plate with the numerals and graduations already imprinted on the face plate. The coating may be sprayed unto the face plate or by other similar methods used in applying paint to a surface. The photoluminescent material is substantially transparent, and thus, transparency is dependent on the thickness of the coating. However, the longevity of the glow is dependent on the particle size, pigment concentration and film thickness. Therefore, the applicable thickness of the coating is a balance between the desired clarity of the numerals and graduations, and the desired longevity of the glow. One skilled in the art would select the appropriate thickness according to the fitness of the particular use.

In one instance, a photoluminescent material such as zinc sulfate is used. In another instance, a material such as Superglow SG05 manufactured by HJ Group, Inc. is used. Superglow SG05 is a photoluminescent material which includes a rare earth element. The characteristic of Superglow SG05 is such that when illuminated for about 10 minutes by a light source such as a 15 watt fluorescent lamp, it can continuously emit light for about 20 hours at a visible luminescent after the light source is removed, gradually attenuating.

In another instance, an aluminum oxide base photoluminescent material, such as Luminova, from United Mineral & Chemical Corporation is used. When the photoluminescent material is applied on the entire face plate of the gauge, the full surface of the gauge face plate glows in the dark enabling medical personnel to easily read the blood pressures of the patient in both outside night emergency situations as well as dark hospital rooms without added light.

Figure 4:
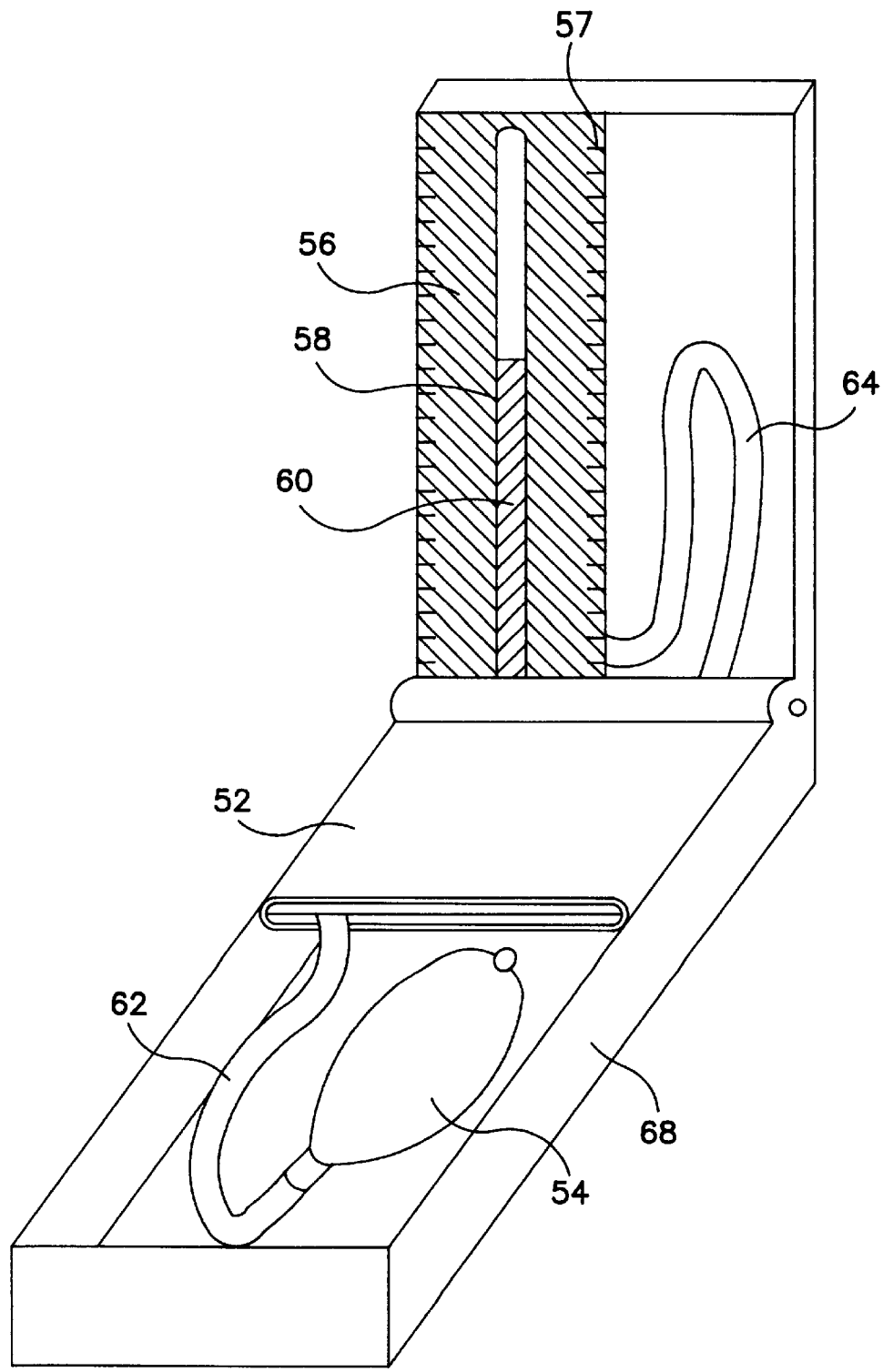
FIG. 4 illustrates another exemplary embodiment of the present invention.

Referring to FIG. 4, if a luminescent ink was used to paint the numbers 57 on the face plate 56 of the desk top mercurial sphygmomanometer, one would not be able to see the rise and fall of the calibrated liquid 60 within the tube 58 in dark situations. However, if the whole face plate 56 was treated with a photoluminescent material depicted by shading, the glow of the face plate 56 would allow easy readings of blood pressures in the dark.

It will be appreciated that although a present embodiment of the invention has been described in detail by way of example, various modifications may be made without departing from the spirit and scope of the invention, which should not be limited except as by the accompanying claims.

We claim:

1. A blood pressure set for measuring a blood pressure comprising:

a aneroid for measuring said blood pressure including a cuff, said cuff being inflatable;

means for inflating said cuff connected to said cuff;

means for displaying a measured blood pressure connected to said cuff, said display means having a face plate; and a photoluminescent material applied on said face plate.

2. The blood pressure set in claim 1, wherein said display means is a gauge.

3. The blood pressure set in claim 1, wherein said display means is a tube filled with a calibrated liquid.

4. The blood pressure set in claim 3, wherein said calibrated liquid is mercury.

5. The blood pressure set in claim 1, wherein said inflating means is a bulb.

6. The blood pressure set in claim 1, wherein said inflating means is an air compressor.

7. The blood pressure set in claim 1, wherein said photoluminescent material includes zinc sulfate.

8. The blood pressure set in claim 1, wherein said photoluminescent material includes aluminum oxide.

9. The blood pressure set in claim 1, wherein said photoluminescent material includes a rare earth element.

10. A gauge for measuring blood pressure comprising:

a hollow body having a surface face plate and a stem for receiving a tube;

an indicator attached to said surface face plate, said indicator in communication with pressure received from said tube; and a photoluminescent material applied on said surface face plate.

11. The gauge in claim 10, wherein said indicator is a rotatable needle.

12. The gauge in claim 10, wherein said indicator is a tube filled with a calibrating liquid.

13. The gauge in claim 10, wherein said calibrated liquid is mercury.

14. The gauge in claim 10, wherein said photoluminescent material includes zinc sulfate.

15. The gauge in claim 10, wherein said photoluminescent material includes aluminum oxide.

16. The gauge in claim 10, wherein said photoluminescent material includes a rare earth element.

* * * * *